(12) United States Patent
Tal et al.

(10) Patent No.: US 7,314,741 B2
(45) Date of Patent: Jan. 1, 2008

(54) ANAEROBIC AMMONIUM OXIDATION FOR WATER TREATMENT IN RECIRCULATING AQUACULTURE

(75) Inventors: Yossi Tal, Baltimore, MD (US); Harold J Schreier, Baltimore, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 501 days.

(21) Appl. No.: 10/493,179

(22) PCT Filed: Oct. 21, 2002

(86) PCT No.: PCT/US02/33608

§ 371 (c)(1),
(2), (4) Date: Jun. 30, 2004

(87) PCT Pub. No.: WO03/032718

PCT Pub. Date: Apr. 24, 2003

(65) Prior Publication Data
US 2005/0087489 A1    Apr. 28, 2005

Related U.S. Application Data

(60) Provisional application No. 60/335,024, filed on Oct. 19, 2001.

(51) Int. Cl.
*C02F 3/00* (2006.01)
(52) U.S. Cl. .................. 435/170; 210/602; 210/615; 210/167.21

(58) Field of Classification Search ................ 210/602, 210/615, 167.21; 435/170
See application file for complete search history.

(56) References Cited

U.S. PATENT DOCUMENTS

| 5,078,884 | A | 1/1992 | Mulder |
| 6,485,646 | B1 * | 11/2002 | Dijkman et al. ............ 210/610 |
| 2002/0074287 | A1 | 6/2002 | Park et al. |

FOREIGN PATENT DOCUMENTS

| JP | 2002-159992 A | 6/2002 |
| WO | WO-98/07664 A1 | 2/1998 |

OTHER PUBLICATIONS

Thamdrup, B. and Dalsgaard, T., "Productions of N2 through Anaerobic Ammonium Oxidation Coupled to Nitrate Reduction in Marine Sediments,".*
Dalsgaard, T., et al., "Factors controlling anaerobic ammonium oxidation with nitrite in marine sediments," Apprlied and Environmental Microbiology, Aug. 2002, p. 3802-3808.*

(Continued)

*Primary Examiner*—Chester T. Barry
(74) *Attorney, Agent, or Firm*—Steven J. Hultquist; Intellectual Property/Technology Law (57) ABSTRACT

Disclosed herein are planctomycetes sp. which convert ammonia to nitrogen under anaerobic conditions, filtration and aquaculture systems comprising said bacteria, filtration media comprising said bacteria, and methods of filtration using said bacteria.

28 Claims, 5 Drawing Sheets

One-stage filtration system

OTHER PUBLICATIONS

Kuenen, J G et al., "Extraordinary anaerobic ammonium-oxidizing bacteria," ASM News, Sep. 2001.*

Kuypers, M M M, "Anaerobic ammonium oxidation by anammox bacteria in the Black Sea," Nature, 422, 608-611 (Apr. 10, 2003).*

Yal, Yossi. et al., Anaerobic Ammonium-Oxidizing (Anammox) Bacteria and Associated Activity in Fixed-Film Biofilters of a Marino . . . Appl. Environ. Microbiol., Apr. 2006, pp. 2896-2904, vol. 72, No. 4.

Daims, H., et al., Novel Nitrospira-like bacteria as dominant nitrite-oxidizers in biofilms from wastewater treatment plants: diversity . . . , Water Science and Technology, 2000, pp. 85-90, vol. 41, No. 4-5.

Hovanec, T.A., et al., Comparative analysis of nitrifying bacteria associated with freshwater and marine aquaria, Appl. Environ. Microbiol., Aug. 1996, pp. 2888-2896, vol. 62, No. 8.

Kloep, Frank, et al., Performance and microbial structure of a nitrifying fluidized-bed reactor , Water Research, Jan. 1, 2000, pp. 311-319, vol. 34, No. 1.

O'Donnell, Anthony G., et al., 16S rDNA methods in soil microbiology , Current Opin. Biotech., Jun. 1999, pp. 225-229, vol. 10, No. 3.

Princic, Alenka, et al., Effects of pH and Oxygen and Ammonium Concentrations on the Community Structure of Nitrifying Bacteria from Wastewater , Appl. Environ. Microbiol., Oct. 1998, pp. 3584-3590, vol. 64, No. 10.

Strous, Marc, et al., Missing lithotroph identified as new planctomycete, Nature, Jul. 29, 1999, pp. 446-449, vol. 400.

Van Rijn, Jaap, The potential for integrated biological treatment systems in recirculating fish culture—A review , Aquaculture, Jan. 15, 1996, pp. 181-201, vol. 139, No. 3-4.

Rusten, B., et al. "Pilot testing and preliminary design of moving bed biofilm reactors for nitrogen removal at the FREVAR wastewater treatment plant." Water Science and Technology, vol. 41, (2000), pp. 13-20.

Rusten, Bjørn, et al. "Moving Bed Biofilm Reactors and Chemical Precipitation for High Efficiency Treatment of Wastewater from Small Communities." Wat. Sci. Tech., vol. 35, (1997), pp. 71-79.

Tal, Yossi, et al. "characterization of the microbial community and nitrogen transformation processes associated with moving bed bioreactors in a closed recirculated mariculture system." Aquaculture. vol. 215, (2003), pp. 187-202.

Megonigal, J.P., M.E. Hines, and P.T. Visscher, 2004, Anaerobic Metabolism: Linkages to Trace Gases and Aerobic Processes, pp. 359-361 in Schlesinger, W.H. (Editor).

* cited by examiner

Figure 1

One-stage filtration system

Figure 2

Two-stage filtration system

Figure 3

```
            851                                                          900
pYT15    ~~~~~~~~~~ ~~~~~~~~~~ ~~~~~~~~~~ ~~~~~~~~~~ ~~~~~~~~~~
plancto  GTAAACGATG GGCACTAAGT AGAGGGGTTT TGATTATCTC TCTGCCGGGA
pYT5     GGCGNAGAGG GGCCGCAACN GNCTAAGTAA TTACGTCGAC CGTGCTGTCC 901                                                          950
pYT15    ~~~~~~~~~~ ~~~~~~~~~~ ~~~~~~~~~~ ~~~~~~~~~~ ~~~~~~~~~~
plancto  TAACGCATTA AGTGCCCCGC CTGGGGAGTA CGGCCGCAAG GCTAAAACTC
pYT5     AAAGGGCTGA CNTTTCGCCC GTCACTCGCG TTGCGTTAAT TACACTCAAT 951                                                         1000
pYT15    ~~~~~~~~~~ ~~~~~~~~~~ ~~~~~~~~~~ ~~~~~~~~~~ ~~~~~~~~~~
plancto  AAAAGAATTG ACGGGGCTC  GCACAAGCGG TGGAGCATGT GGCTTAATTC
pYT5     CGAGTGAGTA ATCCGTGGGG TCCGAAATGT GAAATACGAA GGCCGAGCAT 1001                                                         1050
pYT15    ~~~~~~~~~~ ~~TACGACTC ACTATAGGGC GAATTGGGCC CTCTAGATGC
plancto  GATGCAACGC GAAGAACCTT ACCGGGGCTT GACATGGTAG AAGTAGAAAC
pYT5     ACAACACACC TTAACACTCG CCTATTGTTA AAGTGTGTCC TTTGTCGATA 1051                                                         1100
pYT15    ATGCTCGAGC GGCCGCCAGT GTGATGGATA TCTGCAGAAT TCGCCCT.TA
plancto  CTGAAAGGGC GACGAACGG  ATCCAGTCCG TAACTATCAC AGGTGTTGCA
pYT5     CTGGTACTAA TGCGGTTCGA ACCATGGCT. CGAGCCTAGG TGATCATTGC 1101                                                         1150
pYT15    TGGCTGTCGT CAGCTCGTGC TGTGAAGTGT CGGGTTAAGT CCCTTAACGA
plancto  TGGCTGTCGT CAGCTCGTGT CGTGAGACGT TGGGTTAAGT CCCCTAACGA
pYT5     CGGCGGTCAC ACGACCTTAA GCGGGAATAC CGACAGCAGT CGAGCACAGC 1151                                                         1200
pYT15    GCGAAACCCC TATCGTTAGT TGCCAGCACG TTAAGGTGGG GACTCTAACG
plancto  GCGAAACCCT TGTCTTTAGT TGCCATCAGG TCGAGCTGGG CACTCTAAAG
pYT5     ACTCTACAGC CCAATTCAGG GAATTGCTCG CTTTGGGAAC AGAGATCAAC 1201                                                         1250
pYT15    AGACTGCCGG CGTTAAGCCG GAGGAAGGTG GGACGACGT  CAAGTCATCG
plancto  AGACTGCTGT CGTCAAGACG GAGGAAGGTG GGATGACGT  CAAGTCATCA
pYT5     GGTCGCGCAA TACCGCCCCT GAGATCTCTC TGACGGCCAC AATTTGGCCT 1251                                                         1300
pYT15    TGGCCCTTAT GCCCAGGGAT GCACACGTGC TACAATGGTA TGGACAGAGG
plancto  TGGCCCTTAT GTCCGGGCT  GCACACGTGC TACAATGGTT GGTACAAAGG
pYT5     CCTTCCACCC CTACTGCAGT TCAGGAGTAC CGGAAATACC GGACCCGACG
```

Figure 3A

```
           1301                                                              1350
   pYT15   GCAGCAAGAC  CGTGAGGTGG  AGCAAATCCC  AAAAACCATG  CCTTAGTTCG
  plancto  GATGCTAAAC  TGTAAAGCGG  AGCGAAACCC  ATAAAACCAA  TCCCAGTTCA
    pYT5   TGTGCAGGAT  GTTACCGCGC  ATGTCTCCCT  TCGCTTGAGC  GCTCTCATTC 1351                                                              1400
   pYT15   GATTGTAGGC  TGAAATTCGC  CTGCATGAAG  TCGGAATCGC  TAGTAATCGC
  plancto  GATTGGAGGC  TGAAACCCGC  CTCCATGAAG  TAGGAATCGC  TAGTAATCGC
    pYT5   GTTTAGGGTT  TTTCGCGCGG  GGTCAAGCCT  AACGTCCGAC  GTTGAGCGGA 1401                                                              1450
   pYT15   GTATCAGCTA  CGACGCGGTG  AATGTGTTCC  TGAGCCTTGT  ACACACCGCC
  plancto  GGATCAG.TA  CGCCGCGGTG  AATATGTTCC  CGAGCCTTGT  ACACACCGCC
    pYT5   CGTACTTCGG  CCTTAGCGAT  CATTAGCACC  CAGTCGTATG  GTGCCACTTA 1451                                                              1500
   pYT15   CGTG
  plancto  CGTC
    pYT5   TACA
```

Figure 4

```
248 AATNTATNCGNTCCCTATAGGG.GAAT..GGGCCTTTAAATGCAT.CTNG 293
    | |:|||:||:: |||||||||  ||||  || ||| || ||||||  ||:|
  1 ATTGTATACGTNTCCTATAGGGCGAATTGGGCCCTCTAGATGCATGCTCG 50

294 AGC.GCCGCCA.TGTGATGG...TATTGCAAATTCNCCNT..GATNA.GC 335
    ||| |||||||  ||||||||   | |     |||||:||:|   |||:| ||
 51 AGCGGCCGCCAGTGTGATGGATATCTGCAGAATTCGCCCTTGGATTAGGC 100

336 ATGCAA...TCGCGGACGGCCCTCCTTC.GGGGGGAGNCCGAGCGGCGTA 381
    ||||||    ||||    | ||||||||| |||||||:|||||||||||
101 ATGCAAGTCGCGCGACGGACCCTCCTTCGGGGGGGAGACCGAGCGGCGTA 150

382 A.GGTGA.TAACGTATGG..TACTTA.CCNTGGGAC.GGGATA.CGCCCG 424
    | ||||| ||||||||||   |||||  ||:|||||| ||||||  ||||||
151 AGGGTGAGTAACGTATGGGTAACTTACCCTTGGGACGGGGATAGCGCCCG 200

425 GAAACGGAC.GTAAT.CCCGATAGCACACATGTATCGCATGGTGGATGTG 472
    |||||||||  |||||  ||||||||||||||||||||||||||||||||||
201 GAAACGGACGGTAATACCCGATAGCACACATGTATCGCATGGTGGATGTG 250

473 TTAAAGGC.GGGATCTTCGG.CCTGTCACCCAGGGAGAGGCCATATCCTA 520
    ||||||||  ||||||||||  ||||||||||||||||||||||||||||||||
251 TTAAAGGCGGGGATCTTCGGACCTGTCACCCAGGGAGAGGCCATATCCTA 300

521 TCAGTTAGTTGGCGA.GTAAC.GCTCACCAAGACTATGAC.GGTAGCCGG 567
    ||||||||||||||||  |||||  |||||||||||||||||  ||||||||||
301 TCAGTTAGTTGGCGAGGTAACGGCTCACCAAGACTATGACGGGTAGCCGG 350

568 ACTGAGAGGGTGACCGGCCACACTGGGACTGAGACACTGCCCAGACTCCT 617
    ||||||||||||||||||||||||||||||||||||||||||||||||||
351 ACTGAGAGGGTGACCGGCCACACTGGGACTGAGACACTGCCCAGACTCCT 400

618 ACGGGAGGCTGCAGTCGAGAATCTTCCGCAATGCGCGCAAGCGTGACGGA 667
    ||||||||||||||||||||||||||||||||||||||||||||||||||
401 ACGGGAGGCTGCAGTCGAGAATCTTCCGCAATGCGCGCAAGCGTGACGGA 450

668 GCGACGCCGCGTGGGCGATGAAGGCCTTCGGGTTGTAAAGCCCTGTTACC 717
    |||||||||||||||||||||||||||||| |||||||||||||||||||
451 GCGACGCCGCGTGGGCGATGAAGGCCTTCCGGTTGTAAAGCCCTGTTACC 500

718 TGCTATGAAAGTCGGGCGGTGAACAGCTGTCCCGGCTGACCTCAGCAGGA 767
    ||||||||||||||||||||||||||||||||||||||||||||  ||:||
501 TGCTATGAAAGTCGGGCGGTGAACAGCTGTCCCGGCTGACCTCCCANGA 550

768 GAGGAAGCACCGGCTAAATACGTGCCAGCAGCCGCGGTAATACGTATGGT 817
    |||||:|||||:  |||||||| ||||  |   ||:|||  |||||  |||||:
551 GAGGANGCACCNCCTAAATAC.TGCCCCCACCNCGGCAATACCTATGGN 599

818 GCGAACGTT 826
    || |||:|
600 GCCAACNTN 608
```

ANAEROBIC AMMONIUM OXIDATION FOR WATER TREATMENT IN RECIRCULATING AQUACULTURE

This application claims the benefit of U.S. Provisional Application No. 60/335,024, filed Oct. 19, 2001, which is incorporated in its entirety by reference.

BACKGROUND OF THE INVENTION

This invention pertains to marine systems using planctomyetes for removal of ammonia under anaerobic conditions.

Understanding the parameters necessary for optimizing biological nitrogen removal filters in recirculated aquaculture systems is an important research area in modern aquaculture. Despite their importance, there is a dearth of information about the identity and ecology of the microorganisms involved in catalyzing nitrogen (N) removal in these systems (van Rijn, 1996). Most studies on N-removing bacteria in recirculated aquaculture filters or wastewater treatment plants have focused on the nitrifying consortia belonging to the β- and α-subdivisions of the *Proteobacteria*, i.e. *Nitrosomonas* sp., *Nitrobacter* sp., and *Nitrospira* sp., that occupy aerobic biofiltration units (Princic et al., 1998; Kloep et al., 2000). For many years the general assumption has been that ammonia- and nitrite-oxidizing species were identical in marine and fresh water environments. Recent innovations in microbial ecology techniques, however, have shown that this is not the case. Using oligonucleotide probes to examine nitrifying bacterial populations associated with freshwater and marine aquaria Hovanec and Delong (1996) found that bacteria responsible for ammonia oxidation, *Nitrosomonas europaea*, appear to be present at high levels in seawater aquaria and at very low levels in freshwater aquaria. Other studies demonstrated that the important nitrite-oxidizing bacteria in fresh and marine environments belong to *Nitrospira* sp. and not to *Nitrobacter* sp. as was previously thought (Daims et al., 2000). Thus, while a small number of studies have begun to examine biological filtration systems used in aquaculture almost no information is available about the specific members that compose the bacterial consortia in aerobic filters and the role that they play in N-removal processes. For example, the involvement of anaerobic ammonia oxidizing (anammox) bacteria (Strous et al., 1999) in contributing to ammonia removal in aerobic biofiltration units has not been examined. The wide range of chemical and physical conditions present in these biofilters as well as the various nutrients that are available for bacterial consumption makes it likely that many key microorganisms have been ignored.

One of the main problems in exploring microbial diversity in complex environments, such as those associated with biological filters, is the fact that many of the important microorganisms cannot be cultivated by traditional methods. The availability of molecular tools, such as those used to analyze 16S ribosomal DNA (rDNA) sequences, have made it possible to explore slow growing or uncultivated bacterial species in different environments (O'Donnell and Gorres, 1999). A moving bed bioreactor (MBB) that is a component of a marine recirculated system was used to survey the bacterial community. This approach provided information about the bacterial diversity in these filters and provided some insight into the roles for different bacterial species in the inorganic nitrogen removal process. This information can be used to enhance the efficiency of these biofilters by optimizing operating conditions to induce a desirable process necessary for closing the nitrogen cycle and releasing the fixed nitrogen back to the atmosphere.

U.S. Pat. Nos. 5,078,884 and 5,259,959 by Mulder describe biological anaerobic denitirification of wastewater by bacteria. Mulder describes a system comprising bacteria for the anammox removal of ammonia from freshwater. No marine bacteria are described and the disclosed system is a freshwater system. U.S. Pat. No. 5,660,142 discloses a water purification system for either a fresh or saltwater fish culture system where ammonia is oxidized by nitrifying bacteria to nitrate and nitrate is reduced to gaseous $N_2$ and short chain volatile fatty acids are oxidized to $CO_2$ by anaerobic bacteria in a fluidized bed reactor. U.S. Pat. No. 5,660,142 does not disclose a system or method comprising any marine anammox bacteria.

BRIEF SUMMARY OF THE INVENTION

The invention is a recirculating marine system where a tank has a recirculating filtration system that contains *Planctomycetes* capable of ammonia removal by the anammox process. Anammox is an anaerobic process where ammonia is oxidized to nitrogen gas using nitrite as an electron acceptor. The planctomycetes may be added to filter beads where they form a film on the surface of the beads or beads containing *Planctomycetes* may be provided. These beads are then used in a recirculating filtration system as part of a recirculating marine system. Furthermore, the filtration system may be used to process marine wastewater containing ammonia.

BRIEF DESCRIPTION OF THE SEVERAL VIEWS OF THE DRAWINGS

FIG. 4. Nucleotide sequence of marine planctomyete 16S ribosomal DNA (Harbor mud).

DETAILED DESCRIPTION OF THE INVENTION

As defined herein, marine planctomycetes are those planctomycetes bacteria which grow in a marine (saltwater) environment. Typical conditions for the planctomycetes in the filter system are: Temperature: 22° C.-25° C.; Salinity: 15 ppt-30 ppt; pH: 7-7.5; Oxygen: 0.01 mg/l-0.2 mg/l.

Water retention time in the filter: 3-5 hours. Variations from the above conditions are possible and can be varied by one of ordinary skill in the art.

As defined herein, a marine system may be any container containing saltwater, such as but not limited to a fish tank, aquaculture marine tank, pond, and seafood processing facility. As defined herein, a substrate may be any suitable surface where *Planctomycetes* can bind. Suitable substrates may include, but are not limited to beads used in a moving bed bioreactor, any porous or non-porous bead.

As defined herein, "isolated" is understood to mean separated from the natural environment.

As defined herein, polynucleotides includes DNA and RNA. High stringency conditions or high stringency hybridization conditions are where polynucleotides are hybridized under the following conditions: 6×SSPE, 5×Denhardt's reagent, 50% formamide, 42° C., 0.5% SDS, 100 µg/ml sonicated denatured calf thymus or salmon sperm DNA. Medium stringency conditions or medium stringency hybridization conditions are where polynucleotides are hybridized under the following conditions: 6×SSPE, 5×Denhardt's reagent, 42° C., 0.5% SDS, 100 µg/ml sonicated denatured calf thymus or salmon sperm DNA. Low stringency conditions or low stringency hybridization conditions are where polynucleotides are hybridized under the following conditions: 6×SSPE, 5×Denhardt's reagent, 30° C., 0.5% SDS, 100 µg/ml sonicated denatured calf thymus or salmon sperm DNA. The formulae for the buffers used for hybridizations are: 20×SSPE: 3.6 M NaCl, 0.2 M phosphate, pH 7.0, 20 mM EDTA. 50×Denhardt's reagent: 5 g FICOLL Type 400, 5 g polyvinylpyrrolidone, 5 g bovine serum albumin and water to 500 ml.

It is recognized in the art of nucleotide hybridization that high, medium and low stringency hybridizations can be performed under a variety of different conditions. The provided conditions for performing nucleotide hybridizations are illustrative of the specific hybridizations for high, medium and low stringency conditions. These hybridization conditions are not intended to limit the disclosed method as one of ordinary skill in the art would recognize that the instant invention is not dependent upon the disclosed hybridization conditions but can be achieved using many other different hybridization conditions.

The disclosed polynucleotides and polynucleotide fragments of the instant invention allow identification of species of marine planctomycetes suitable for ammonia removal according to the instant invention. Methods of identification are known in the art and include PCR, hybridization assays and polynucleotide sequencing.

A preferred embodiment of the instant invention is a marine system comprising a recirculating filter system comprising marine planctomycetes having anammox activity. A further preferred embodiment is a marine system comprising a recirculating filter system comprising marine planctomycetes having anammox activity wherein the system is a one-stage filtration system. Yet another preferred embodiment is a marine system comprising a recirculating filter system comprising marine planctomycetes having anammox activity wherein the system is a two-stage filtration system. Another preferred embodiment is a marine filtration system comprising a filter apparatus wherein the filter apparatus contains marine planctomycetes having anammox activity. A preferred embodiment of the instant invention is a method of removing ammonia from a marine system comprising contacting the ammonia containing saltwater with marine planctomycetes. A further preferred embodiment is a method of removing ammonia from saltwater comprising contacting the ammonia containing saltwater with marine planctomycetes. Yet a further embodiment is a method of removing ammonia wherein the planctomycetes are bound to a substrate.

A preferred embodiment of the invention is an isolated marine Planctomycete having anammox activity. A further preferred embodiment is a Planctomycete, wherein the isolates is pYT15 or pYT5. A preferred embodiment is an isolated Planctomyce, wherein the bacteria comprise polynucleotide comprising the sequence as set forth in SEQ ID NO: 1, 2 or 3. Yet a further embodiment is a Planctomycete, wherein the polynucleotide comprise at least a 20 nucleotide fragment of SEQ ID NO: 1. Yet a further preferred embodiment is a Planctomycete comprising a nucleotide fragment of SEQ ID NO: 1 that is at least 22 nucleotides in length. Still a further preferred embodiment is a Planctomycete comprising a nucleotide fragment of SEQ ID NO: 1 that is at least 24 nucleotides in length. A preferred embodiment is a *Planctomycetes* comprising a polynucleotide wherein the polynucleotide comprises at least a 6 nucleotide fragment of SEQ ID NO: 2. A preferred embodiment is a *Planctomycetes* comprising a polynucleotide wherein the polynucleotide comprises at least an 8 nucleotide fragment of SEQ ID NO: 2. A preferred embodiment is a *Planctomycetes* comprising a polynucleotide wherein the polynucleotide comprises at least a 10 nucleotide fragment of SEQ ID NO: 2.

A preferred embodiment of the instant invention is an isolated polynucleotide comprising the nucleotide sequence as set forth in SEQ ID NO: 1, 2 or 3. Another preferred embodiment of the instant invention is an isolated polynucleotide fragment comprising at least 20 contiguous nucleotides of SEQ ID NO: 1. A further preferred embodiment is a polynucleotide fragment comprising at least 22 contiguous nucleotides of SEQ ID NO: 1. Another preferred embodiment of the instant invention is an isolated polynucleotide fragment comprising at least 6 contiguous nucleotides of SEQ ID NO: 2. Yet another preferred embodiment of the instant invention is an isolated polynucleotide fragment comprising at least 8 contiguous nucleotides of SEQ ID NO: 2. Another preferred embodiment of the instant invention is an isolated polynucleotide fragment comprising at least 6 contiguous nucleotides of SEQ ID NO: 3 or SEQ ID NO: 4. Still another preferred embodiment of the instant invention is a polynucleotide fragment wherein the fragment comprises at least 8 contiguous nucleotides of SEQ ID NO: 3 or SEQ ID NO: 4. A preferred embodiment of the instant invention is an isolated polynucleotide which hybridizes under high stringency hybridization conditions to SEQ ID NOs: 1, 2, 3 or 4. Another preferred embodiment of the instant invention is an isolated polynucleotide which hybridizes under medium stringency hybridization conditions to SEQ ID NOs: 1, 2, 3 or 4. A preferred embodiment of the instant invention is an isolated polynucleotide which hybridizes under high stringency hybridization conditions to at least a 6 nucleotide fragment of SEQ ID NO: 1 and wherein the polynucleotide is not SEQ ID NO: 5 or a fragment thereof. Another preferred embodiment of the instant invention is an isolated polynucleotide which hybridizes under high stringency hybridization conditions to at least a 6 nucleotide fragment of SEQ ID NOs: 1, 2, 3 or 4. Still another preferred embodiment of the instant invention is an isolated *Planctomycetes* comprising an isolated polynucleotide which hybridizes under high stringency hybridization conditions to SEQ ID NOs: 1, 2, 3 or 4.

EXAMPLE 1

Aquaculture facilities and filter setup. Nitrifying MBBs connected to recirculated marine systems in the Center of Marine Biotechnology's Aquaculture Research Center were used for these studies. A 5 m$^3$ pond containing gilthead seabream, Sparus aurata, was operated at a density of 80 kg/m$^3$ and feeding rate of 6 kg/day. The pond was connected to a 2 m$^3$ MBB filled with 1 m$^3$ of polyethylene beads having a specific surface area of 500 m$^2$/m$^3$ (4.86 cm$^2$/bead) (Waste Management Technologies, Inc., Baton Rouge, La. USA). A flow rate of 2.5 m$^3$/hr was set to enable two exchanges of pond water per hour through the filter. After four months of operation, 3000 beads from the MBB were transferred to a small experimental salt water system having a filter volume of 5 L and tank volume of 150 L. The system was operated without any organic load under aerobic conditions with water retention time similar to the original system. Ammonium chloride was added to the system daily to maintain a constant ammonia-nitrogen ($NH_3$—N) concentration of 5 mg/l.

EXAMPLE 2

Batch experiments. Batch experiments were performed using 200 beads removed from low or high organic load filter systems, which were incubated in 250 ml flasks under different conditions. For nitrification activity, incubations were performed under aerobic conditions with the addition of 3 mg $NH_3$—N/l. Denitrification activity was examined by incubating filters under anaerobic conditions with 130 mg nitrate-nitrogen ($NO_3$—N)/l with and without 10 mM sodium acetate. Anammox activity was induced under anaerobic conditions with 7 mg $NH_3$—N/l and 7 mg nitrite-nitrogen ($NO_2$—N)/l without additional carbon source. All incubations were repeated at least three times at different time intervals in a synthetic sea water medium with a final salinity of 20 ppt at 26° C.

EXAMPLE 3

Figure 1:
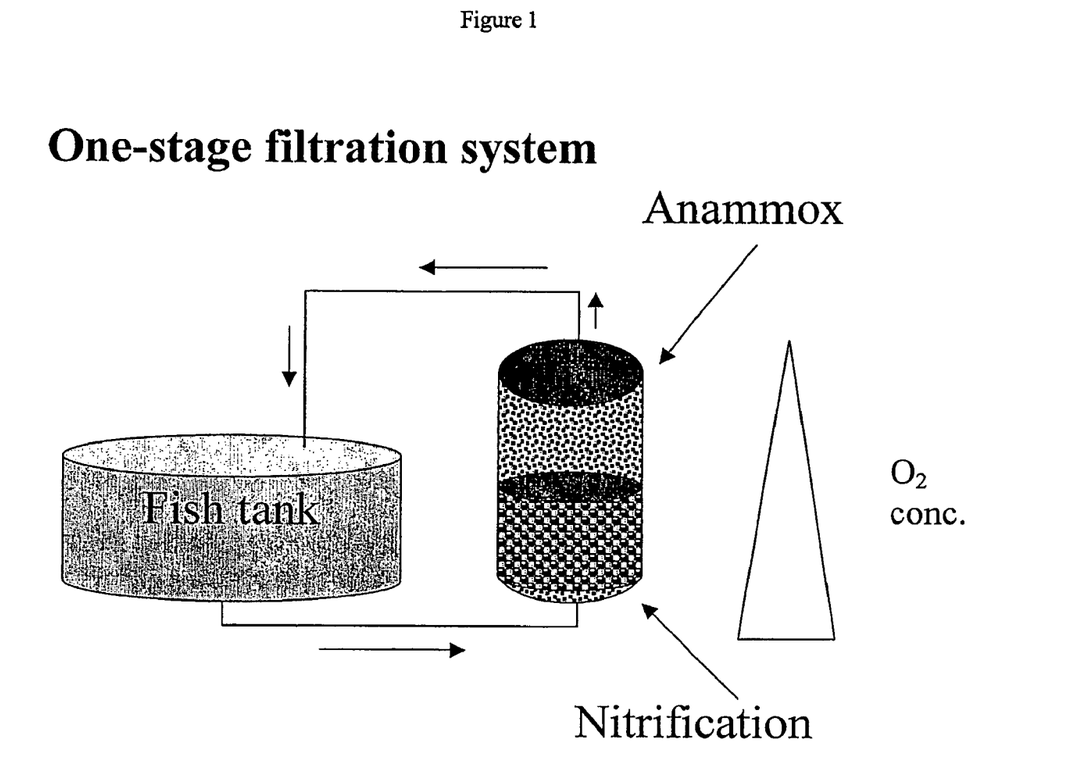
FIG. 1. Marine aquaculture system with a one-stage filtration system. Anammox and nitrification reactions are carried out by different bacterial species under different oxygen levels, all in the same filter.

The One-step process includes a submerged fixed film bead bed filter. This approach exploits the fact that nitrifiers and anammox bacteria co-exist, sharing the same microbial biofilm. Operating the filter with a sharp oxygen gradient where the lower part of the filter is oxygenated allows ammonia oxidizing bacteria to convert some of the ammonia to nitrite, while the upper part of the filter operates under anaerobic condition to activate the anammox organisms, which oxidize the remaining ammonia to nitrogen gas using nitrite as an electron acceptor. In this "one-step process" the water from the fish tank flows through one filter where complete autotrophic ammonia removal takes place via two processes. Oxygen levels in the upper and lower portions of the filter are controlled by controlling the oxygen concentration of the inlet water and the retention time of the water in the filter.

EXAMPLE 4

Figure 2:
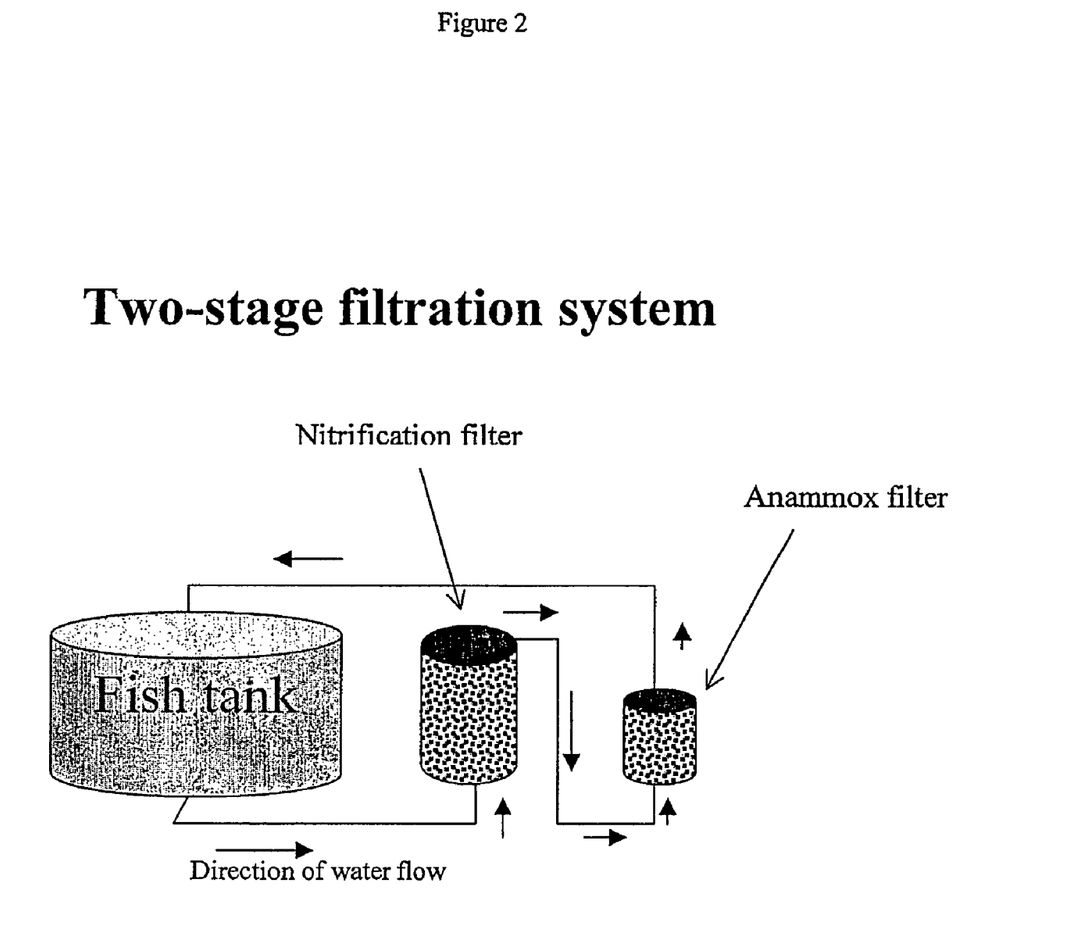
FIG. 2. Marine aquaculture system with a two-stage filtration system. Anammox and nitrification reactions are carried out by different bacterial species under different oxygen levels in different filters.
Figure 3A:
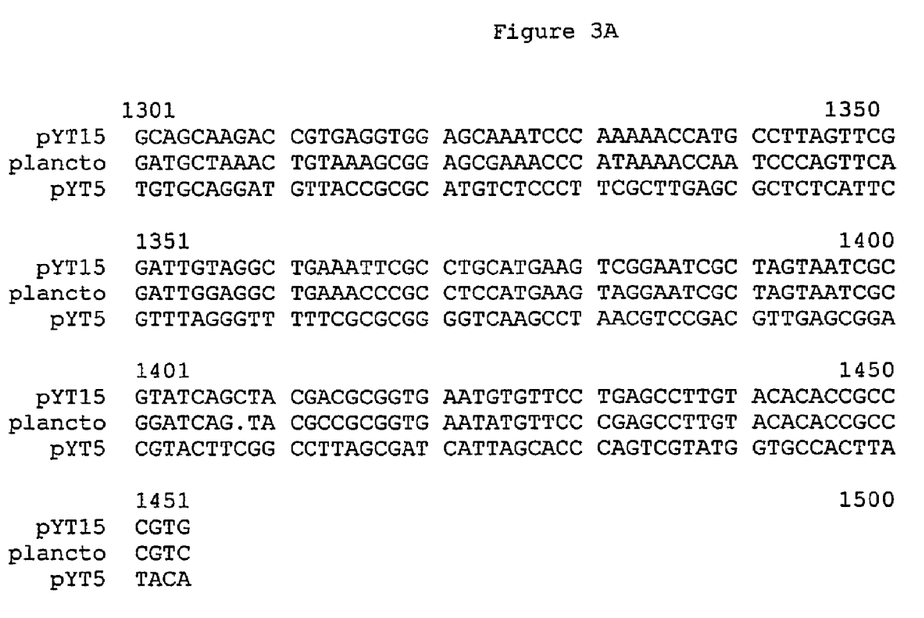
FIG. 3. Nucleotide sequence of marine planctomyete 16S ribosomal DNA (pYT15 and pYT5). Plancto is 16S ribosomal DNA with GenBank Accession No. AJ131819.

The two stage filter setup comprises two submerged fixed film bead bed filters where nitrification and anammox occur separately. The first filter operates under aerobic conditions and low water retention times to promote ammonia-oxidizing bacteria to oxidize ammonia to nitrite. In the second filter the anammox process is induced by anaerobic conditions and by the continuous supply of water rich in ammonia and nitrite. Water from the fish tank circulates through the first aerobic filter for ammonia oxidation, with subsequent processing through the second stage filter for complete nitrogen removal by the anammox bacteria.

Depending upon the volume of the tanks used, the condition of the water in the tanks, the size of the filters, etc., more than one or combinations of the one- and two-stage filtration systems may be used. Furthermore, the filter systems described above may be used to remove ammonia from ammonia-containing seawater, allowing such seawater to be returned to a body of saltwater without introducing ammonia. These examples are provided for illustration of the instant invention and are not intended to limit the scope of the disclosed invention.

We claim:

1. A marine system comprising a recirculating filter system comprising marine planctomycetes having anammox activity.

2. The marine filtration system according to claim 1 further comprising a filter apparatus wherein the filter apparatus contains the marine planctomycetes having anammox activity.

3. The marine system of claim 1, wherein the filter system is a one-stage filtration system.

4. The marine system of claims 1, wherein the filter system is a two-stage filtration system.

5. The filtration system of claim 1, wherein the marine Planctomycetes comprise polynucleotide comprising the sequence as set Forth in SEQ ID NO: 1, 2 or 3.

6. The filtrations system of claim 2, wherein the marine Planctomycetes comprise polynucleotide comprising the sequence as set forth in SEQ ID NO: 1, 2 or 3, wherein the system is a two-stage filtration system.

7. A method of removing ammonia from a marine system comprising contacting the ammonia containing saltwater with marine planctomycetes.

8. The method of removing ammonia according to claim 7, wherein the marine system comprises salt water.

9. The method of claim 7, wherein the planctomycetes are bound to a substrate.

10. The method according to claim 7, wherein the marine Planctomycetes anammox activity.

11. The method according to claim 10, wherein the Planctomycetes are pYT15 or pYT15.

12. The method according to claim 7, wherein the Planctomycete comprise polynucleotide comprising the sequence as set forth in SEQ ID NO: 1, 2 or 3.

13. The method according to claim 12, wherein the Planctomycetes comprise at least a 20 nucleotide fragment of SEQ ID NO: 1.

14. The method according to claim 12, wherein the the nucleotide fragment is at least 22 nucleotides in length.

15. The method according to claim 12, wherein the wherein the nucleotide fragment is at least 24 nucleotides in length.

16. The method according to claim 12, wherein the polynucleotide comprise at least a 6 nucleotide fragment of SEQ ID NO: 2.

17. The method according to claim 16, wherein the the nucleotide fragment is at least 8 nucleotides in length.

18. An isolated marine Planctomycetes having anammox activity.

19. The isolated marine Planctomycetes having anammox activity according to claim 18 comprising the nucleotide sequence as set forth in SEQ ID NO: 1, 2 or 3.

20. The isolated marine Planctomycetes having anammox activity according to claim 18 comprising at least 20 contiguous nucleotides of SEQ ID NO: 1.

21. The isolated marine Planctomycetes having anammox activity according to claim 18 comprising at least 22 contiguous nucleotides of SEQ ID NO: 1.

22. The isolated marine Planctomycetes having anammox activity according to claim 18 comprising at least 6 contiguous nucleotides of SEQ ID NO: 2.

23. The isolated marine Planctomycetes having anammox activity according to claim 18 comprising at least 8 contiguous nucleotides of SEQ ID NO: 2.

24. An isolated polynucleotide fragment comprising at least 6 contiguous nucleotides of SEQ ID NO: 3 or SEQ ID NO: 4.

25. The isolated polynucleotide fragment according to claim 24 of wherein the fragment comprises at least 8 contiguous nucleotides of SEQ ID NO: 3 or SEQ ID NO: 4.

26. An isolated polynucleotide which hybridizes under high stringency hybridization conditions to SEQ ID NOs. 1, 2, 3 or 4.

27. The isolated polynucleotide according to claim 26, wherein the polynucleotide is SEQ ID NO. 1.

28. An isolated polynucleotide which hybridizes under high stringency hybridization conditions to at least a 6 nucleotide fragment of SEQ ID NO: 1 and wherein the polynucleotide is not SEQ ID NO: 5 or a fragment thereof.

* * * * *

UNITED STATES PATENT AND TRADEMARK OFFICE
CERTIFICATE OF CORRECTION

PATENT NO. : 7,314,741 B2 Page 1 of 1
APPLICATION NO. : 10/493179
DATED : January 1, 2008
INVENTOR(S) : Yossi Tal et al.

It is certified that error appears in the above-identified patent and that said Letters Patent is hereby corrected as shown below:

Column 9, line 60, "set Forth" should be -- set forth --.

Signed and Sealed this

Sixth Day of May, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 441
<212> TYPE: DNA
<213> ORGANISM: Planctomyces sp.

<400> SEQUENCE: 1

```
tacgactcac tatagggcga attgggccct ctagatgcat gctcgagcgg ccgccagtgt      60
gatggatatc tgcagaattc gcccttatgg ctgtcgtcag ctcgtgctgt gaagtgtcgg     120
gttaagtccc ttaacgagcg aaacccctat cgttagttgc cagcacgtta aggtggggac     180
tctaacgaga ctgccggcgt taagccggag gaaggtgggg acgacgtcaa gtcatcgtgg     240
cccttatgcc cagggatgca cacgtgctac aatggtatgg acagagggca gcaagaccgt     300
gaggtggagc aaatcccaaa aaccatgcct tagttcggat tgtaggctga aattcgcctg     360
catgaagtcg gaatcgctag taatcgcgta tcagctacga cgcggtgaat gtgttcctga     420
gccttgtaca caccgcccgt g                                               441
```

<210> SEQ ID NO 2
<211> LENGTH: 603
<212> TYPE: DNA
<213> ORGANISM: Planctomyces sp.

```
<220> FEATURE:
<221> NAME/KEY: misc_feature
<222> LOCATION: (1)..(603)
<223> OTHER INFORMATION: N = a, t, g or c

<400> SEQUENCE: 2
ggcgnagagg ggccgcaacn gnctaagtaa ttacgtcgac cgtgctgtcc aaagggctga      60
cntttcgccc gtcactcgcg ttgcgttaat tacactcaat cgagtgagta atccgtgggg     120
tccgaaatgt gaaatacgaa ggccgagcat acaacacacc ttaacactcg cctattgtta     180
aagtgtgtcc tttgtcgata ctggtactaa tgcggttcga accatggctc gagcctaggt     240
gatcattgcc ggcggtcaca cgaccttaag cgggaatacc gacagcagtc gagcacagca     300
ctctacagcc caattcaggg aattgctcgc tttgggaaca gagatcaacg gtcgcgcaat     360
accgcccctg agatctctct gacggccaca atttggcctc cttccacccc tactgcagtt     420
caggagtacc ggaaataccg gacccgacgt gtgcaggatg ttaccgcgca tgtctcccctt    480 cgcttgagcg ctctcattcg tttagggttt tcgcgcggg gtcaagccta acgtccgacg      540
ttgagcggac gtacttcggc cttagcgatc attagcaccc agtcgtatgg tgccacttat     600
aca                                                                  603

<210> SEQ ID NO 3
<211> LENGTH: 608
<212> TYPE: DNA
<213> ORGANISM: Planctomyces sp.
<220> FEATURE:
<221> NAME/KEY: misc_feature
<222> LOCATION: (1)..(608)
<223> OTHER INFORMATION: n = a, t, g, or c

<400> SEQUENCE: 3
attgtatacg tntcctatag ggcgaattgg gccctctaga tgcatgctcg agcggccgcc      60
agtgtgatgg atatctgcag aattcgccct tggattaggc atgcaagtcg cgcgacggac     120
cctccttcgg gggggagacc gagcggcgta agggtgagta acgtatgggt aacttaccct     180
tgggacgggg atagcgcccg gaaacggacg gtaatacccg atagcacaca tgtatcgcat     240
ggtggatgtg ttaaaggcgg ggatcttcgg acctgtcacc cagggagagg ccatatccta     300
tcagttagtt ggcgaggtaa cggctcacca agactatgac gggtagccgg actgagaggg     360
tgaccggcca cactgggact gagacactgc ccagactcct acgggaggct gcagtcgaga     420
atcttccgca atgcgcgcaa gcgtgacgga gcgacgccgc gtgggcgatg aaggccttcc     480
ggttgtaaag ccctgttacc tgctatgaaa gtcgggcggt gaacagctgt cccggctgac     540
ctccccanga gaggangcac cncctaaata ctgcccccca ccncggcaat acctatgggng    600 ccaacntn                                                             608

<210> SEQ ID NO 4
<211> LENGTH: 579
<212> TYPE: DNA
<213> ORGANISM: Planctomyces sp.
<220> FEATURE:
<221> NAME/KEY: misc_feature
<222> LOCATION: (1)..(579)
<223> OTHER INFORMATION: n = a, c, g, or c

<400> SEQUENCE: 4
aatntatncg ntccctatag gggaatgggc ctttaaatgc atctngagcg ccgccatgtg      60
atggtattgc aaattcnccn tgatnagcat gcaatcgcgg acggccctcc ttcggggga     120
```

-continued

```
gnccgagcgg cgtaaggtga taacgtatgg tacttaccnt gggacgggat acgcccggaa    180
acggacgtaa tcccgatagc acacatgtat cgcatggtgg atgtgttaaa ggcgggatct    240
tcggcctgtc acccagggag aggccatatc ctatcagtta gttggcgagt aacgctcacc    300
aagactatga cggtagccgg actgagaggg tgaccggcca cactgggact gagacactgc    360
ccagactcct acgggaggct gcagtcgaga atcttccgca atgcgcgcaa gcgtgacgga    420
gcgacgccgc gtgggcgatg aaggccttcg ggttgtaaag ccctgttacc tgctatgaaa    480
gtcgggcggt gaacagctgt cccggctgac ctcagcagga gaggaagcac cggctaaata    540
cgtgccagca gccgcggtaa tacgtatggt gcgaacgtt                           579
```

<210> SEQ ID NO 5
<211> LENGTH: 603
<212> TYPE: DNA
<213> ORGANISM: Planctomyces sp.
<220> FEATURE:
<221> NAME/KEY: misc_feature
<222> LOCATION: (1)..(603)
<223> OTHER INFORMATION: n = a, c, g, or t

<400> SEQUENCE: 5

```
gtaaacgatg ggcactaagt agagggtttt tgattatctc tctgccggga taacgcatta     60
agtgccccgc ctggggagta cggccgcaag gctaaaactc aaaagaattg acggggggctc   120 gcacaagcgg tggagcatgt ggcttaattc gatgcaacgc gaagaacctt accggggctt    180
gacatggtag aagtagaaac ctgaaagggc gacgaacggt atccagtccg taactatcac    240
aggtgttgca tggctgtcgt cagctcgtgt cgtgagacgt tgggttaagt cccctaacga    300
gcgaaaccct tgtctttagt tgccatcagg tcgagctggg cactctaaag agactgctgt    360
cgtcaagacg gaggaaggtg gggatgacgt caagtcatca tggcccttat gtcccgggct    420
gcacacgtgc tacaatggtt ggtacaaagg gatgctaaac tgtaaagcgg agcgaaaccc    480
ataaaaccaa tcccagttca gattggaggc tgaaacccgc ctccatgaag taggaatcgc    540
tagtaatcgc ggatcagtac gccgcggtga atatgttccc gagccttgta cacaccgccc    600
gtc                                                                  603
```